(12) United States Patent
Offord Cavin et al.

(10) Patent No.: US 8,299,034 B2
(45) Date of Patent: Oct. 30, 2012

(54) NUTRITIONAL COMPOSITIONS FOR PROMOTION OF BONE GROWTH AND MAINTENANCE OF BONE HEALTH COMPRISING EXTRACTS OF FOR EXAMPLE ROSEMARY OR CARAWAY

(75) Inventors: Elizabeth Offord Cavin, Montreux (CH); Gary Williamson, Harrogate (GB); Didier Courtois, St-Avertin (FR); Bernard Lemaure, Tours (FR); Andre Touche, Monts (FR); Grace Ing Soon, Singapore (SG); Laurent Ameye, Lausanne (CH)

(73) Assignee: Nestec S.A., Vevey (CH)

( * ) Notice: Subject to any disclaimer, the term of this patent is extended or adjusted under 35 U.S.C. 154(b) by 143 days.

(21) Appl. No.: 12/919,157

(22) PCT Filed: Feb. 25, 2008

(86) PCT No.: PCT/EP2008/052251
§ 371 (c)(1),
(2), (4) Date: Aug. 24, 2010

(87) PCT Pub. No.: WO2009/106121
PCT Pub. Date: Sep. 3, 2009

(65) Prior Publication Data
US 2011/0028416 A1    Feb. 3, 2011

(51) Int. Cl.
*A61K 31/70*    (2006.01)
*A61K 31/35*    (2006.01)
*A61K 31/235*    (2006.01)
(52) U.S. Cl. .......... 514/27; 514/453; 514/456; 514/533
(58) Field of Classification Search .............. 514/27, 514/453, 456, 533
See application file for complete search history.

(56) References Cited

U.S. PATENT DOCUMENTS
6,242,012 B1    6/2001    Newmark et al.

FOREIGN PATENT DOCUMENTS
WO    WO2007/113291    10/2007

OTHER PUBLICATIONS

B. Klausen, et al., "Effect of longovital treatment on development of periodontal disease in rats," Scandinavian Journal of Dental Research, vol. 101, No. 1, Jan. 1, 1993, pp. 33-36, XP009085438.
C.J. Edwards, et al. "Oral statins and increased bone-mineral density in postmenopausal women," The Lancet, vol. 355, Issue 9222, Jun. 24, 2000, pp. 2218-2219.
G. Mundy, et al., "Stimulation of Bone Formation in Vitro and in Rodents by Statins," Science, Dec. 3, 1999, vol. 286, pp. 1946-1949.
P. Wang, et al., "HMG-CoA Reductase Inhibitors and the Risk of Hip Fractures in Elderly Patients," JAMA, vol. 286, 2000, pp. 3211-3216.
International Search Report for International Application No. PCT/EP2008/052251 mailed on Nov. 18, 2008.
Written Opinion for International Application No. PCT/EP2008/052251 mailed on Nov. 18, 2008.

*Primary Examiner* — Raymond Henley, III
(74) *Attorney, Agent, or Firm* — K&L Gates LLP (57) ABSTRACT

Compositions and methods for maintenance of bone health or prevention, alleviation and/or treatment of bone disorders are presented. The present invention also provides the manufacture of a nutritional product, a supplement or a medicament for promoting bone growth or for the maintenance of bone health and methods regarding same. In an embodiment, the present invention provides a composition comprising an active ingredient having an effective amount of a plant or plant extract containing at least one phytochemical having the ability to induce bone morphogenic protein expression.

18 Claims, 12 Drawing Sheets

NUTRITIONAL COMPOSITIONS FOR PROMOTION OF BONE GROWTH AND MAINTENANCE OF BONE HEALTH COMPRISING EXTRACTS OF FOR EXAMPLE ROSEMARY OR CARAWAY

The present invention generally relates to new compounds and to nutritional compositions that provide health benefits. More specifically, the present invention relates to beneficial compositions that can be used, for example, to improve bone density and formation and/or to induce bone morphogenic protein expression. Embodiments of the present invention relate to compounds in accordance with claim 1 and to a use in accordance with claim 3.

Bone mass evolves throughout life and is regulated by genetic, mechanical and hormonal mechanisms. Bone mineral acquisition occurs during childhood and peak bone mass is achieved around 20 years of age. During this period, bone formation exceeds bone resorption. Later in life, and particularly around the time of the menopause, or in the elderly population, bone mass and quality are impaired due to a higher bone turnover with excessive bone resorption leading to a gradual loss of bone mass, microarchitecture, structure and strength. To maintain bone, it is important to restore the balance between bone formation and bone resorption. This bone remodeling process is regulated at the bone cell level involving a tight interaction between bone forming cells (osteoblasts) and bone resorbing cells (osteoclasts).

Phytonutrients, especially flavonoids, can positively influence the bone remodeling process. The most reported data is for the soy isoflavones which, in some studies, have been shown to prevent bone loss and improve bone mineral density (BMD) in postmenopausal women at doses of 50-90 mg/day. However, not all studies with isoflavones are positive and controversy still exists over their efficacy. Further, some epidemiological evidence exists for benefits of tea as a previous study showed that tea drinkers had a higher mean BMD than non tea-drinkers in an elderly population, however no intervention studies have been carried out to substantiate this finding.

Currently, there is a strong interest in identifying agents which can stimulate bone formation. The delivery of recombinant BMP-2 has been shown to induce bone or cartilage formation. For example, bone morphogenic protein 2 (BMP-2) is a member of the TGFβ family and is a key regulator of bone growth during embryonic development, and further bone growth and repair. Statins (effective drugs for cholesterol-lowering through inhibition of the enzyme HMG-CoA reductase) improve bone formation, partly mediated by induction of BMP-2 (G. Mundy, et al., Science 286: 1946-1949 (1999); C. J. Edwards, et al., Lancet, 355: 2218-2219 (2000)). Statins were also able to reduce hip fracture risk in menopausal women (P. S. Wang, et al., JAMA 283 :3211-3216 (2000)).

The present invention generally relates to compositions for maintenance of bone health or prevention, alleviation and/or treatment of bone disorders. The present invention also provides 6"-Feruloylnepitrin, 6"-Coumaroylnepitrin, and a compound with the following formula Peak-ID II
New
C-0063-W-06 dehydroxy rosmarinic acid, which may be used in the compositions of the present invention. Embodiments of the present invention relate to the manufacture of a nutritional product, a supplement or a medicament for promoting bone growth or for the maintenance of bone health and methods regarding same. In particular, the present invention provides the manufacture of a nutritional product, a supplement or a medicament for promoting bone formation which is important for bone growth as well as for the maintenance of bone health through balanced bone remodeling and methods regarding same.

In an embodiment, the present invention provides the use of a composition comprising at least one new compound and/or at least one polyphenol of the present invention for the preparation of a product to induce bone morphogenic protein expression. The at least one polyphenol is preferably selected from the group consisting of 6"-Feruloylnepitrin, 6"-Coumaroylnepitrin, dehydroxy rosmarinic acid, eupafolin, carnosol, scutellarin, genkwanin, kaempferol, acacetin, genkwanin, or mixtures thereof, and may be provided in the form of a plant extract.

Hence, in an embodiment, the present invention provides a composition comprising an active ingredient having an effective amount of at least one new compound and/or at least one polyphenol of the present invention, having the ability to induce bone morphogenic protein expression. The composition may further inhibit bone resorption.

The product may be a medicament, a food product, nutritional supplement and/or nutraceutical for humans and/or pets. Preferably, the product comprises the at least one polyphenol in an amount of 0.001-100 wt.-% of the total dry weight of the composition. The at least one polyphenol may be to be administered in an amount of 0.01 μg-100 mg per kg body weight per day.

The product may further comprise a protein source, a fat source and/or a carbohydrate source. The protein source may provide about 1-55% of the total energy of the product, the fat source may provide about 5-55% of the total energy of the product, and the carbohydrate source may provide about 40-80% of the total energy of the product.

The product may be intended for oral and/or enteral application.

Preferably, the product may be in a form selected from the group consisting of a nutritionally balanced food, a nutritionally complete formula, a dietary supplement, a dairy product, a chilled or shelf stable beverage, a soup, a nutritional bar, pet food, confectionery, a pharmaceutical composition and combinations thereof.

The product prepared by the use of the present invention may be used to treat or prevent osteoporosis, to modulate the ratio of bone formation and/or bone resorption, to inhibit bone resorption, to assist bone regeneration during fracture healing, to increase bone formation and bone mineral density during growth, to optimize peak bone mass or to decrease bone loss, in particular bone loss associated with age in humans or pets and/or to improve bone density.

In an alternative embodiment, the present invention provides a method for manufacturing a food composition for the prevention, the alleviation and/or the treatment of bone disorders or maintenance of bone health in humans or pets, the method comprising providing a food composition; and adding to the food composition an active ingredient having an effective amount of at least one new compound and/or at least one polyphenol of the present invention, having the ability to stimulate bone morphogenic protein and/or inhibit bone resorption to prepare the composition. For example, the composition can include components chosen from the group consisting of chicory, tea, cocoa, bioactives, antioxidants, fatty acids, prebiotic fibers, glucosamine, chondroitin sulphate and combinations thereof.

In another embodiment, the present invention provides a method for the treatment, alleviation or prevention of a bone disorder or the maintenance of bone health, the method comprising administering a therapeutically-effective amount of a composition comprising an active ingredient having an effective amount of at least one new compound and/or at least one polyphenol of the present invention, having the ability to induce bone morphogenic protein expression to an individual in need of same.

In an alternative embodiment, the present invention provides a method of increasing bone formation, bone mineral density during growth and optimize peak bone mass in humans or pets, the method comprising feeding an individual, a composition comprising an active ingredient having an effective amount of at least one new compound and/or at least one polyphenol of the present invention, having the ability to induce bone morphogenic protein expression.

In still another embodiment, the present invention provides a method of treating or preventing osteoporosis, the method comprising administering to an individual having or at risk of osteoporosis a therapeutically effective amount of a composition comprising an active ingredient having an effective amount of at least one new compound and/or at least one polyphenol of the present invention, having the ability to induce bone morphogenic protein expression in the individual.

In yet an alternative embodiment, the present invention provides a method of stimulating bone regeneration during fracture healing, the method comprising feeding an individual having a fracture, a therapeutically-effective amount of a composition comprising an active ingredient having an effective amount of at least one new compound and/or at least one polyphenol of the present invention, having the ability to induce bone morphogenic protein expression in the individual.

In a further embodiment, the present invention provides a method of decreasing bone loss, the method comprising feeding an individual exhibiting a bone loss, a composition comprising an active ingredient having an effective amount of at least one new compound and/or at least one polyphenol of the present invention having the ability to induce bone morphogenic protein expression in the individual.

Additional features and advantages of the present invention are described herein, and will be apparent from the following detailed description, the figures and the examples.

The present invention relates to beneficial compositions that can be used, for example, to improve bone density and formation and methods regarding same. For example, in an embodiment, the present invention is directed to polyphenols that stimulate bone formation and improve bone maintenance. The polyphenols may be obtained from plant sources and may be provided in the form of plant extracts.

In plants, a number of isoprenoids (monoterpenes, sesquiterpenes, etc.) were found to be modulators of both HMG-CoA reductase and protein prenylation, mechanisms probably linked to either the bone resorption inhibition or bone formation enhancement. Therefore, certain plant compounds can be potential inhibitors of bone resorption and/or enhancers of bone formation.

In embodiments of the present invention, extracts comprising the polyphenols of the present invention were prepared from edible and/or medicinal plant species having a potential to stimulate BMP-2 and bone formation. As discussed in more detail later, the extracts were generally prepared by a 4-step process (a) hexane, (b) methanol-water, (c) methanol-water extracts hydrolyzed with glycosidases and re-extracted with ethylacetate, and (d) removal of large polyphenols with a PVPP column. The methanol-water and ethylacetate extracts were used for in vitro screening. Extracts were hydrolyzed by α- and β-glycosidases instead of acid to ensure the release of flavonoid aglycones (the biologically active form) from their glycosides.

The following bioassays were used for bone formation analysis

BMP-2 gene reporter assay (high throughput screen)
Alkaline phosphatase in osteoblast cells
Calvaria organ culture in vitro, bone formation
Injection into calvaria in vivo, bone formation.

For example, extracts were screened for bone formation by a high throughput gene reporter assay for BMP-2 followed by an alkaline phosphatase assay and an organ culture model and finally by injection into mice calvaria in vivo. Subfractions of positive extracts and/or pure compounds were further tested for activity. Analysis of the chemical composition of one active extract was performed in order to determine the active compounds.

It was surprisingly found that, e.g., compounds extracted from rosemary plants could be used as active compounds for bone development, growth and/or maintenance. For example, at the following phenolic compounds were found to have an anabolic potential: 6"-Feruloylnepitrin, 6"-Coumaroylnepitrin, dehydroxy rosmarinic acid, eupafolin, carnosol, scutellarin, genkwanin, kaempferol, acacetin and/or genkwanin. The rosemary plant extracts and the pure compounds were tested in an osteoblast/osteoclast co-culture system. The rosemary extract as well as, e.g., eupafolin, carnosol and scutellarein were shown to have an activity for regulation of the key cytokines controlling bone remodeling, i.e. OPG/RANKL. Furthermore, it was found that carnosol stimulates osteopontin (OPN) expression in human osteoblast cells, possibly via AP-1/Nrf-2 signaling pathways.

Three new active polyphenols were identified, and have to the inventors knowledge never been described in the literature.

These are 6"-Feruloylnepitrin, 6'-Coumaroylnepitrin and a compound with the following formula Peak-ID II
New
C-0063-W-06 dehydroxy rosmarinic acid.

In an embodiment of the present invention, the new compounds and/or polyphenols of the present invention are obtained from methanol/water extracts of the rosemary plant (25% of the initial leaf dry matter) obtained after a defatting step with hexane contain the molecules responsible for the activity and could be used in a food product. Their in vitro activity was observed both, in the initial methanol/water extract and as pure compounds. A high activity is observed in a BMP-2 assay after purification/concentration through ethyl acetate extraction and/or hydrolysis with glucosidase and subsequent ethyl acetate extraction. Since the activity of the pure compounds is significantly higher than the activity in the initial MeOH/water extracts, it is preferred if plant extracts used in accordance with the present invention are enriched in the polyphenols of the present invention. It is preferred if the concentration of the polyphenols of the present invention in the enriched plant extract is at least 2 fold, preferably 10 fold, even more preferred at least 50-fold compared to their content in the MeOH/water extracts described above. Compared to the natural plant the content of the polyphenols of the present invention in the enriched extract is preferably at least 10 fold increased, preferably at least 100 fold increased, even more preferred at least 500-fold increased.

The new compounds and polyphenols of the present invention, or plants or plant extracts comprising them, in particular rosemary plants or plant extracts, may be used in the preparation of a food composition. The composition may be in the form of a nutritionally balanced food or pet food, a dietary supplement, a treat or a pharmaceutical composition.

The new compounds and polyphenols may be used alone or in association with other compounds, plants or plant extracts such as chicory, tea, cocoa, or with one or more other bioactive molecules such as antioxidants, fatty acids, prebiotic fibers, glucosamine, chondroitin sulphate, for example.

In one embodiment of the present invention, a food composition or a nutritional formula for human consumption is prepared. This composition may be a nutritional complete formula, a dairy product, a chilled or shelf stable beverage, a soup, a dietary supplement, a meal replacement, a nutritional bar or confectionery.

A nutritional formula prepared by the use of the present invention may comprise a source of protein. Dietary proteins are preferably used as a source of protein. The dietary proteins may be any suitable dietary protein; for example animal proteins (such as milk proteins, meat proteins and egg proteins); vegetable proteins (such as soy protein, wheat protein, rice protein, and pea protein); mixtures of free amino acids; or combinations thereof. Milk proteins such as casein, whey proteins and soy proteins are particularly preferred. The composition may also contain a source of carbohydrates and a source of fat.

If the nutritional formula includes a fat source, the fat source preferably provides about 5% to about 55% of the energy of the nutritional formula; for example about 20% to about 50% of the energy. The lipids making up the fat source may be any suitable fat or fat mixtures. Vegetable fats are particularly suitable; for example soy oil, palm oil, coconut oil, safflower oil, sunflower oil, corn oil, canola oil, lecithins, and the like. Animal fats such as milk fats may also be added if desired.

A source of carbohydrate may be added to the nutritional formula. It preferably provides about 40% to about 80% of the energy of the nutritional composition. Any suitable carbohydrates may be used, for example sucrose, lactose, glucose, fructose, corn syrup solids, and maltodextrins, and mixtures thereof. Dietary fiber may also be added if desired. If used, it preferably comprises up to about 5% of the energy of the nutritional formula. The dietary fiber may be from any suitable origin, including for example soy, pea, oat, pectin, guar gum, gum arabic, and fructooligosaccharides. Suitable vitamins and minerals may be included in the nutritional formula in an amount to meet the appropriate guidelines.

One or more food grade emulsifiers may be incorporated into the nutritional formula if desired; for example diacetyl tartaric acid esters of mono- and di-glycerides, lecithin and mono- and di-glycerides. Similarly suitable salts and stabilizers may be included. Vitamins and minerals may also be combined with the plant extract.

The nutritional composition is preferably enterally administrable; for example in the form of a powder, tablet, capsule, a liquid concentrate, solid product or a ready-to-drink beverage. If it is desired to produce a powdered nutritional formula, the homogenized mixture is transferred to a suitable drying apparatus such as a spray drier or freeze drier and converted to powder.

In another embodiment, a nutritional composition comprises a milk-based cereal together with a prebiotic formulation. Preferably the milk-based cereal is an infant cereal which acts as a carrier for the prebiotic formulation.

In another embodiment, a food product may be enriched with at least one compound, plant or plant extract according to the present invention. For example, a fermented milk, a yoghurt, a fresh cheese, a renneted milk, a confectionery article, a sweet or sweetened beverage, a confectionery bar, breakfast cereal flakes or bars, drinks, milk powders, soy-based products, non-milk fermented products or nutritional supplements for clinical nutrition.

The amount of the new compounds and/or polyphenols of the present invention, and—if present—plant or plant extract in the composition may vary according to its source and its utilization. In a preferred embodiment, an efficient daily dose amount is of at least about 1 mg, and more preferably from 1 mg to 200 mg of the active molecule per day.

In an alternative embodiment, a pharmaceutical composition containing at least a new compound and/or a polyphenol of the present invention, as described above, in an amount sufficient to achieve the desired effect in an individual can be prepared. This composition may be a tablet, a liquid, capsules, soft capsules, pastes or pastilles, gums, or drinkable solutions or emulsions a dried oral supplement, a wet oral supplement. The pharmaceutical composition can further contain carriers and excipients that are suitable for delivering the respective active molecule of different nature to the target tissue. The kind of the carrier/excipient and the amount thereof will depend on the nature of the substance and the mode of drug delivery and/or administration contemplated. It will be appreciated that the skilled person will, based on his own knowledge select the appropriate components and galenic form.

The new compound and/or polyphenol according to the invention may be used in the preparation of a pet food composition. The said composition may be administered to the pet as a supplement to its normal diet or as a component of a nutritionally complete pet food, and more preferably in a hypocaloric pet food. It may also be a pharmaceutical composition for pets.

The new compound and/or polyphenol according to the invention may be used alone or in association with other plants such as chicory, tea, cocoa, or with other bioactive molecules such as antioxidants, fatty acids, prebiotic fibers, glucosamine, chondroitin sulphate, for example.

Preferably, a pet food composition prepared in accordance with the present invention contains about 0.01 to 100 mg of the compounds and/or polyphenols per gram of dry pet food. The nutritionally complete pet food composition according to the invention may be in powdered, dried form, a treat or a wet, chilled or shelf stable pet food product. It may be chilled or provided as a shelf stable product. These pet foods may be produced by ways known in the art.

The pet food may optionally also contain a prebiotic, a probiotic microorganism or another active agent, for example a long chain fatty acid. The amount of prebiotic in the pet food is preferably less than 10% by weight. For example, the prebiotic may comprise about 0.1% to about 5% by weight of the pet food. For pet foods which use chicory as the source of the prebiotic, the chicory may be included to comprise about 0.5% to about 10% by weight of the feed mixture; more preferably about 1% to about 5% by weight.

If a probiotic micro-organism is used, the pet food preferably contains about $10^4$ to about $10^{10}$ cells of the probiotic micro-organism per gram of the pet food; more preferably about $10^6$ to about $10^6$ cells of the probiotic micro-organism per gram. The pet food may contain about 0.5% to about 20% by weight of the mixture of the probiotic micro-organism; preferably about 1% to about 6% by weight; for example about 3% to about 6% by weight.

If necessary, the pet food can be supplemented with minerals and vitamins so that they are nutritionally complete. Further, various other ingredients, for example, sugar, salt, spices, seasonings, flavoring agents, and the like may also be incorporated into the pet food as desired.

In another embodiment, dietary adjuncts may be prepared so as to improve pet food quality. As dietary adjuncts, they may be encapsulated or may be provided in powder form and packaged in conjunction with or separately from a main meal, be it wet or dry. By way of example, a powder containing extracts according to the invention, may be packed in sachets in a powder form or in a gel or lipid or other suitable carrier. These separately packaged units may be provided together with a main meal or in multi-unit packs for use with a main meal or treat, according to user instructions.

Administering to a human or animal, the food or pet food composition as described above, results in improved bone regeneration during fracture healing. It helps to stimulate bone formation and bone mineral density during growth and optimize peak bone mass. In particular, it provides an optimal bone growth during childhood. This food composition helps to prevent bone loss, in particular bone loss associated with age in mammals or bone loss associated with long term hospitalization. It reduces the risk of developing osteoporosis and improves recovery after fracture. Furthermore, it helps to build cartilage in mammals and prevents osteoarthritis in pets and humans, which results in a better activity and/or mobility of the individual (e.g. pets and/or humans).

It is clear to those of skill in the art that they can freely combine all features as disclosed herein without departing from the scope of the invention as disclosed.

Further advantages and features of the present invention will be apparent from the examples and figures.

EXAMPLES

By way of example and not limitation, the following examples are illustrative of various embodiments of the present invention and further illustrate experimental testing conducted in accordance with embodiments of the present invention.

Example 1

(Source) of Spice Extracts Rich in Polyphenols

Some polyphenols are found in rosemary or caraway extracts

TABLE 1

| Source of spice extracts rich in polyphenols | | | |
|---|---|---|---|
| NAME | GENERA | SPECIES | ORGAN |
| Rosemary | *Rosmarinus* | *officinalis* | leaves |
| Caraway | *Carum* | *carvi* | seeds |
| Thyme | *Thymus* | *vulgaris* | leaves |
| Spearmint | *Mentha* | *spicata* | leaves |

Plant Extraction Procedure

Figure 1:
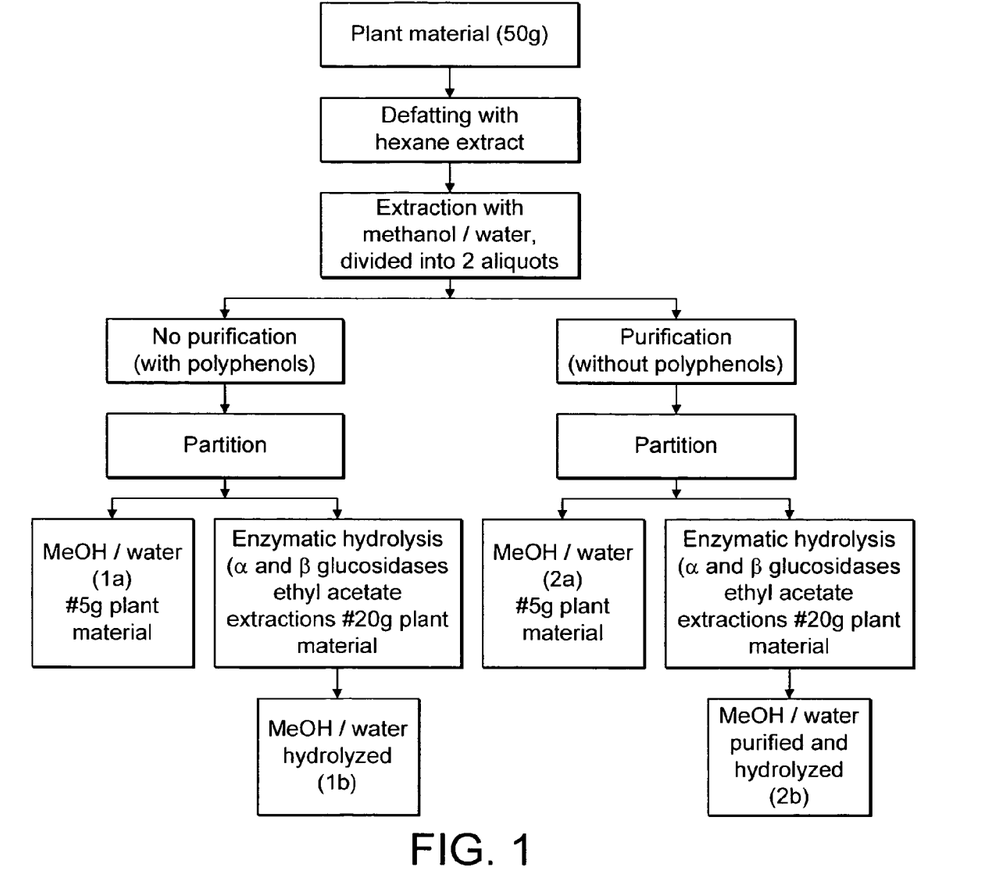
FIG. 1 illustrates an extraction protocol.

Referring to FIG. 1, the extraction procedure generally included the following steps:

Hexane, defatting (extracts not screened)

MeOH/H$_2$O (1a)

MeOH/H$_2$O, hydrolyzed with α, β-glycosidases, extracted with ethylacetate (1b)

1a purified on PVPP column to remove high mol wt polyphenols (2a)

1b purified on PVPP column to remove high mol wt polyphenols (2b)

Extracts 2a and 2b gave similar results as the extracts 1a and 1b. The extraction procedure included glycosidase treatment (instead of acid hydrolysis) to ensure conversion of flavonoid glycosides to aglycones.

Figure 2:
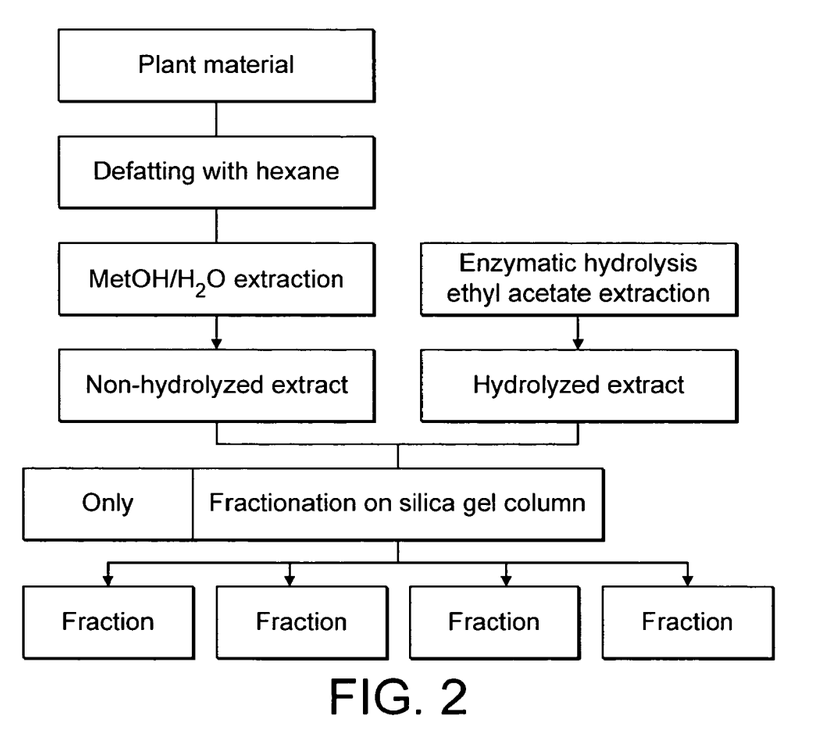
FIG. 2 illustrates a summary of the extraction procedure and first fractionation.

Subfractionation—Four subfractions were prepared by fractionation on silica gel cartridge with elution by solvents of varying polarity: ethyl acetate then ethyl acetate/methanol (95/5) followed by ethyl acetate/methanol (50/50) and finally methanol (FIG. 2).

Screening Steps and Bioassays

The screening for bone formation was carried out in several stages:

(i) BMP-2 high throughput gene reporter assay of non-hydrolyzed MeOH/H$_2$O extracts (1a) and corresponding glycosidase hydrolyzed extract in ethyl acetate (1b). Extracts were tested twice at concentrations of 1 to 100 µg/ml, diluted in culture medium from plant extract stocks prepared as 50 mg/ml in DMSO.

(ii) Extracts positive in the BMP-2 screen were prepared de novo and screened again with dose-response to confirm "hits".

(iii) BMP-2 testing of subfractionation of positives/hits and candidate pure compounds (iv) Compounds shown positive in the BMP-2 assay were further tested for osteoblast differentiation using the alkaline phosphatase assay and in an organotypic model of bone formation using a culture of calvarial bones and histomorphometry for demonstration of bone formation as described by Traianedes et al, (1998).

(v) Final injection in vivo of "hit" compounds into mouse calvaria bones and monitoring of bone area and thickness. Extracts were assessed in a 4-day in vitro neonatal murine calvarial assay. Bones were incubated with the extracts for the entire 4 days.

(vi) Resorption activity monitored by measuring the amount of type I collagen released in the media as osteoclasts digest bone.

Results: Plant Extract Screening in BMP-2 Gene Reporter & Organ Culture

Extracts from the spices *Rosmarinus officinalis, Carum carvi, Thymus vulgaris, Mentha spicata* were positive in 2 rounds of BMP-2 screening.

These active extracts or subfractions were further confirmed to stimulate bone formation in the calvaria organ culture model:

TABLE 2

Summary of spice extracts positive in BMP-2 screen and confirmed in organ culture

| Latin name English name | Part | Extract | BMP-2 positive extracts | Organ culture |
|---|---|---|---|---|
| *Rosmarinus officinalis* rosemary | Leaves | MeOH/H$_2$O ethylacetate | 2004, 2127 2005, 2089 | 2004 2005 |
| *Carum carvi* caraway | Seeds | ethylacetate | 2074 | 2074 |
| *Thymus vulgaris* (thyme) | Leaves | ethylacetate | 2067 | 2067 |
| *Mentha spicata* Spearmint | Leaves | ethylacetate | 2072 | 2072 |

Conclusions of Plant Extract Screening

BMP-2 hits confirmed in organ culture bone formation assay were for example extracts of rosemary leaves, thyme leaves, spearmint leaves, caraway seeds.

Figure 3A:
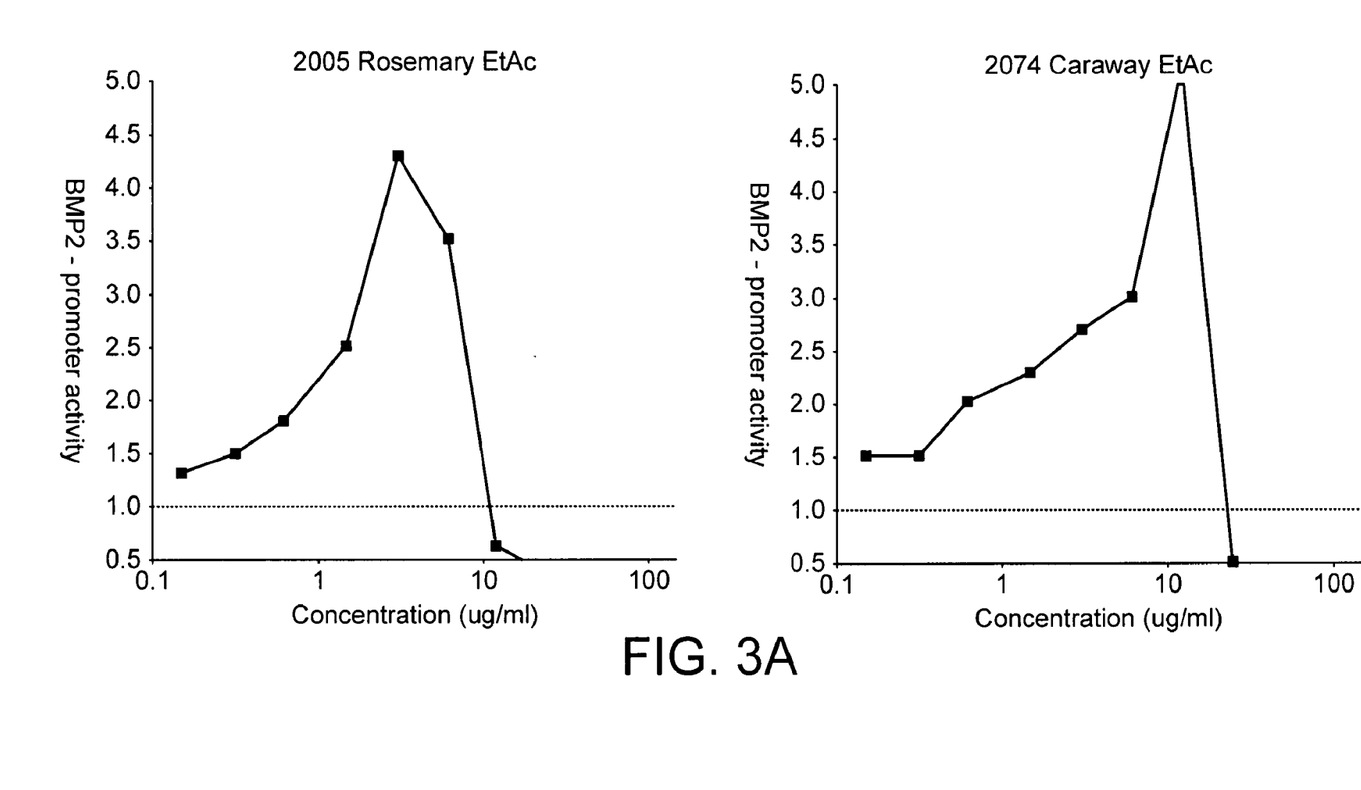
FIG. 3A illustrates BMP-2 results for rosemary and caraway extracts.
Figure 3B:
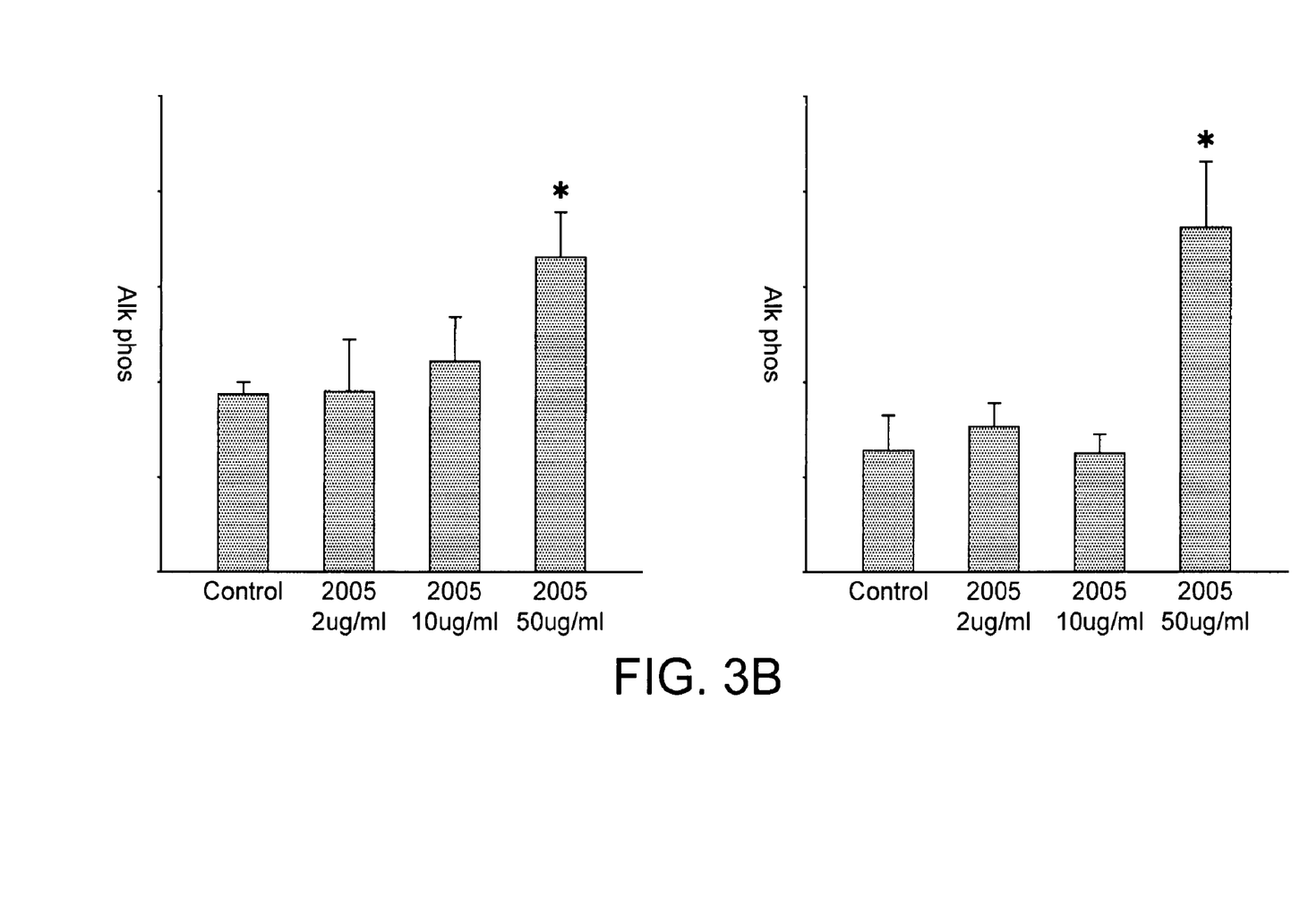
FIG. 3B illustrates alkaline phosphatase results for rosemary and caraway extracts.
Figure 3C:
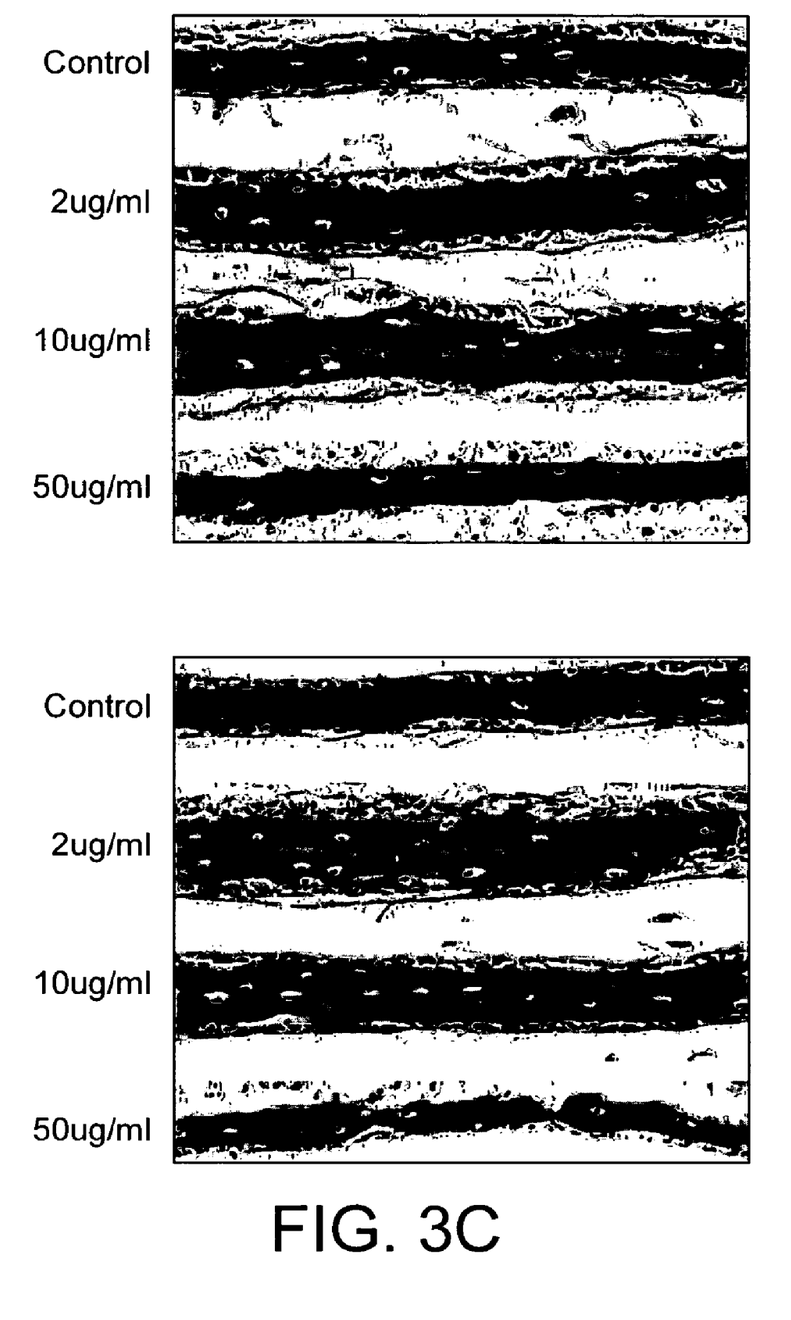
FIG. 3C illustrates bone formation in organ culture for rosemary and caraway extracts.

Example of Rosemary & Caraway Hits for BMP-2 Activity, Confirmed in Alkaline Phosphatase Assay and Organ Culture FIGS. 3A-C illustrate bone formation assay results for rosemary and caraway extracts.

Effect of Extraction Procedure on BMP-2 Activity

Figure 4:
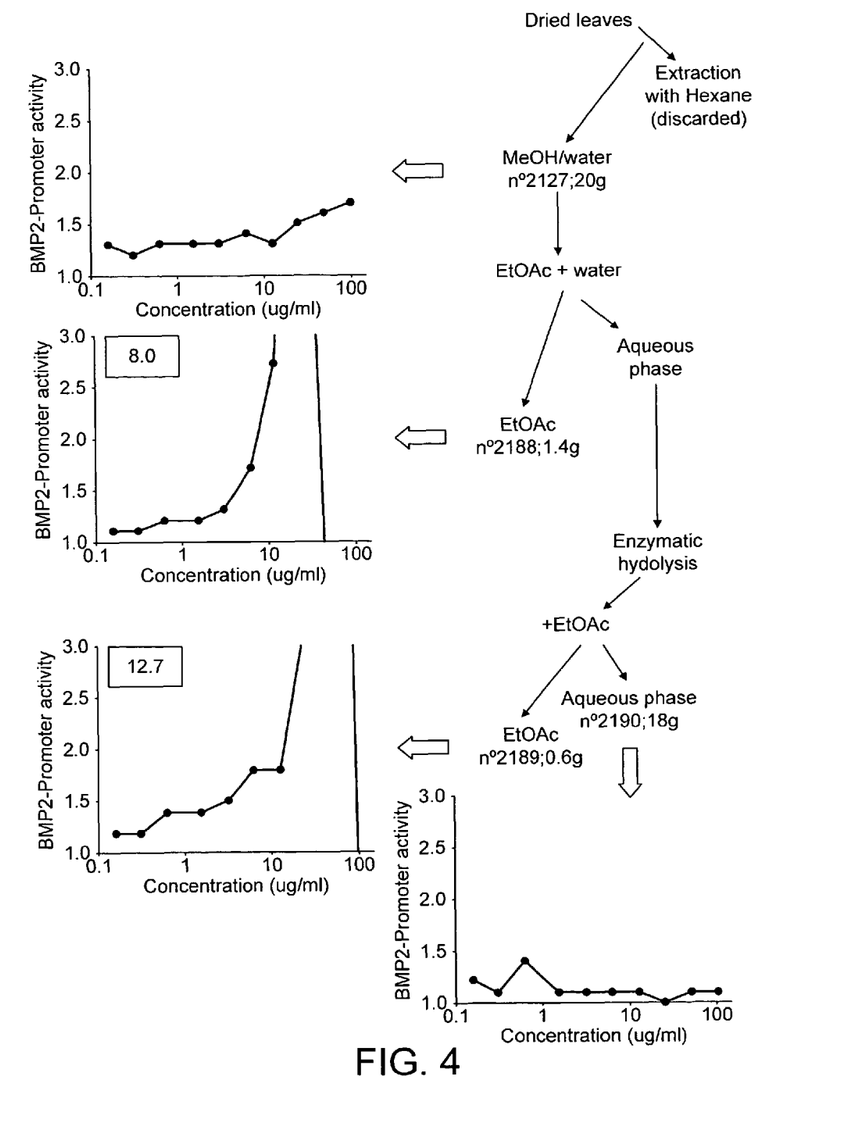
FIG. 4 illustrates an extraction procedure using an initial methanol/water extract, and BMP-2 activity of the extracts (from 80 g dried leaves (hexane=6 g)).

After a first extraction of rosemary with methanol/water on previously defatted leaves (ext. 2127), the induction of BMP-2 gene expression was 1.5× at 10 µg/ml (FIG. 4). A specific extraction of this extract, with ethyl acetate (2188), led to an increase in BMP-2 expression (8× induction). This suggests that the EtOAc extraction process resulted in the concentration of the active compounds from the original MeOH/water extract. After hydrolysis with glycosidases, the resulting ethyl acetate (2189) extract is also active, showing that additional active molecules have been extracted. Extract 2189 is even slightly more active than the non-hydrolyzed one.

These results show unambiguously an activity in both extracts (non hydrolyzed: 2188 and hydrolyzed: 2189) suggesting the existence of active molecules under two forms: free and/or bound (glycosylated) in the original extract.

Bone Formation in Calvaria Following Injection In Vivo

Figure 5:
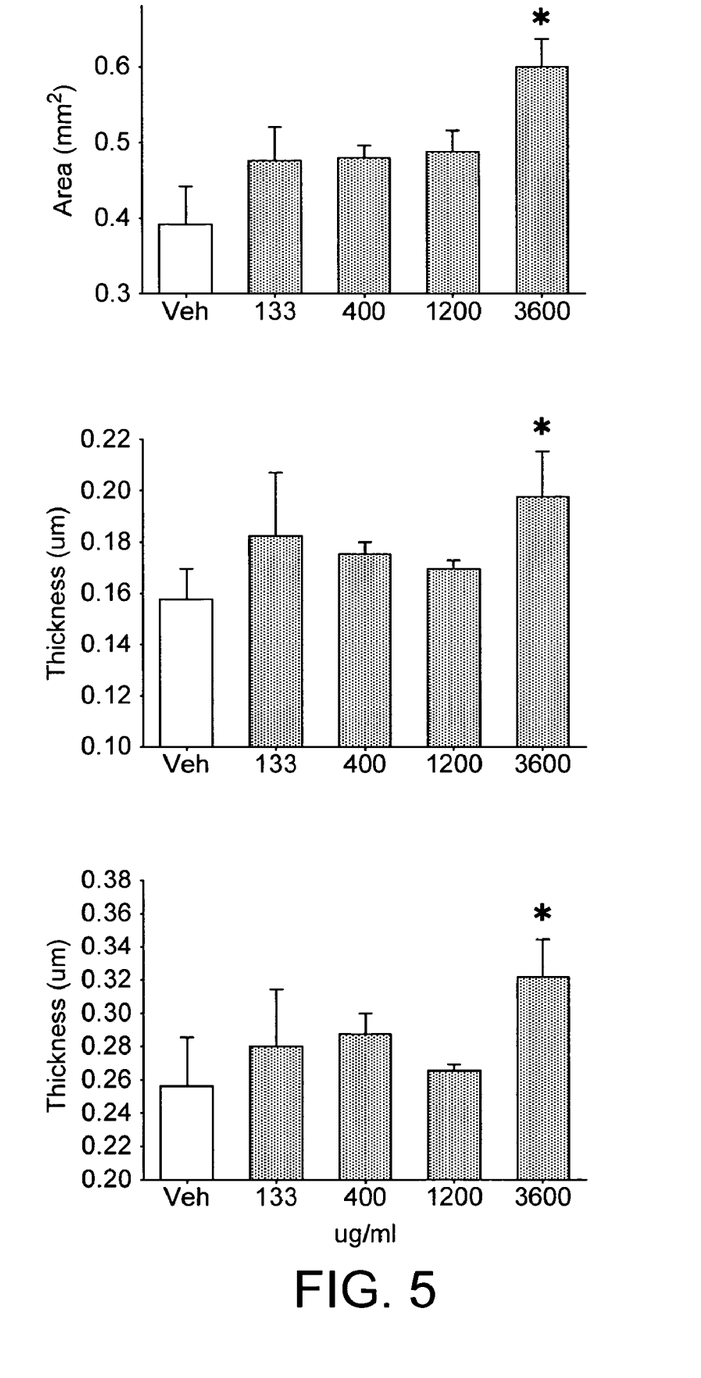
FIG. 5 illustrates bone formation in vivo with rosemary extract.

*Rosmarinus officinalis*(rosemary extract) shows bone formation activity in 3 independent bone formation in vitro assays (BMP-2, alkaline phosphatase, bone organ culture) as well as in the calvaria in vivo assay (see FIG. 5).

The rosemary extract (here the leaves were extracted first with water, and water extract was hydrolyzed then extracted with ethyl acetate) is injected into murine calvaria head, followed by ex vivo bone formation analysis ÷

Pure Compounds Screening

Phenolics were tested at concentrations of 1-10 µM

Figure 6A:
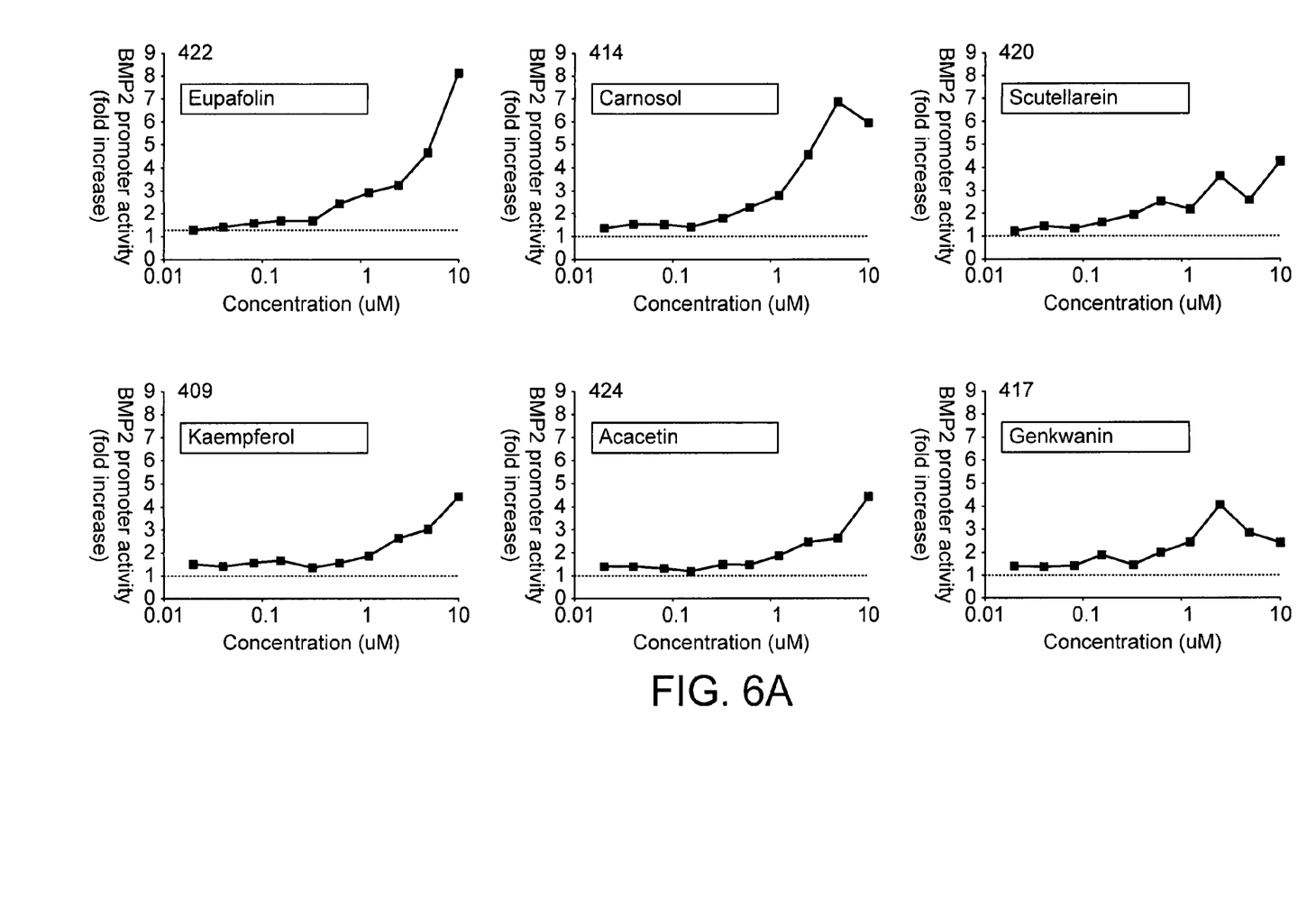
FIG. 6A illustrates phenolics found positive in BMP-2 assay.
Figure 6B:
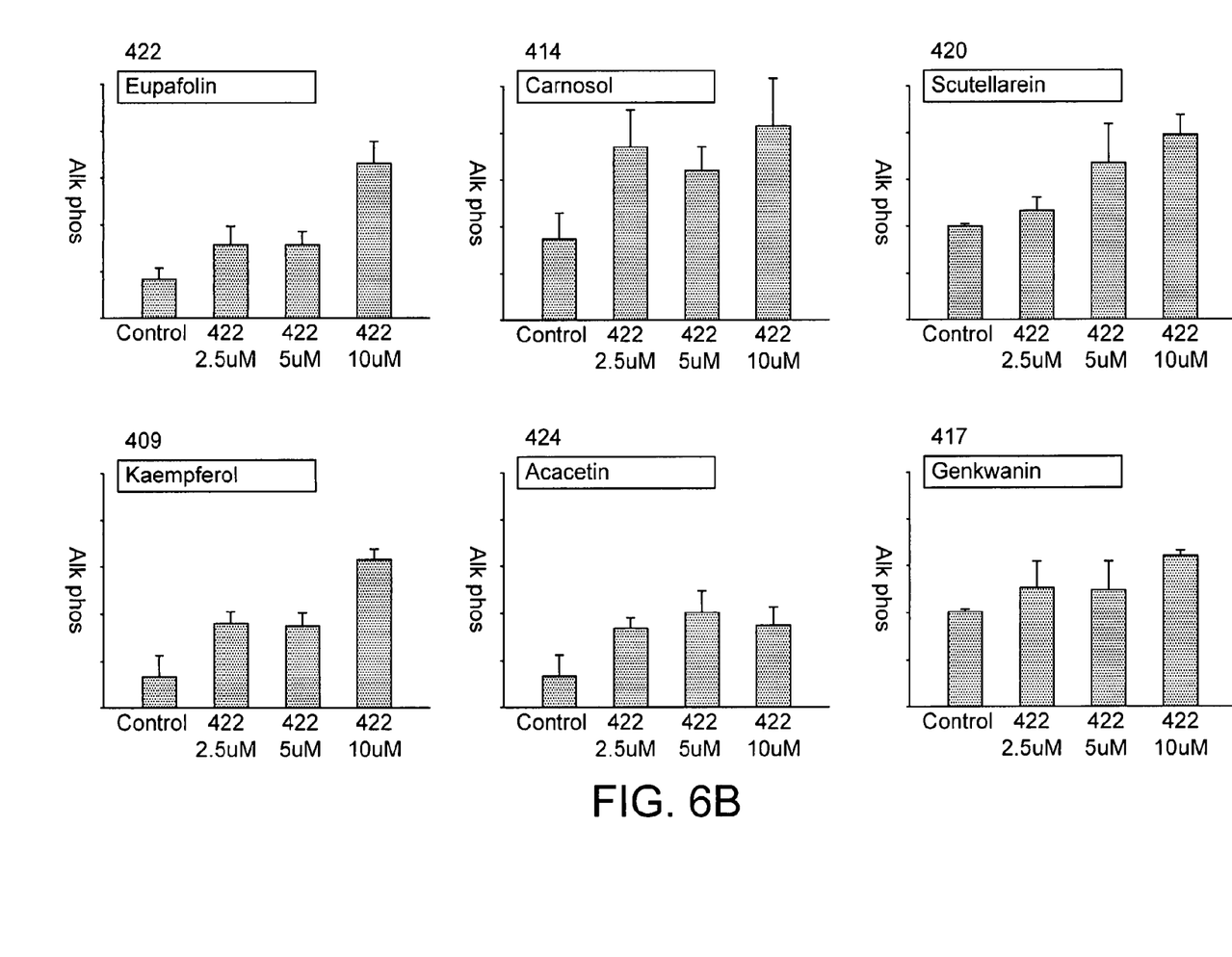
FIG. 6B illustrates an alkaline phosphatase assay of BMP-2 positive phenolics.
Figure 6C:
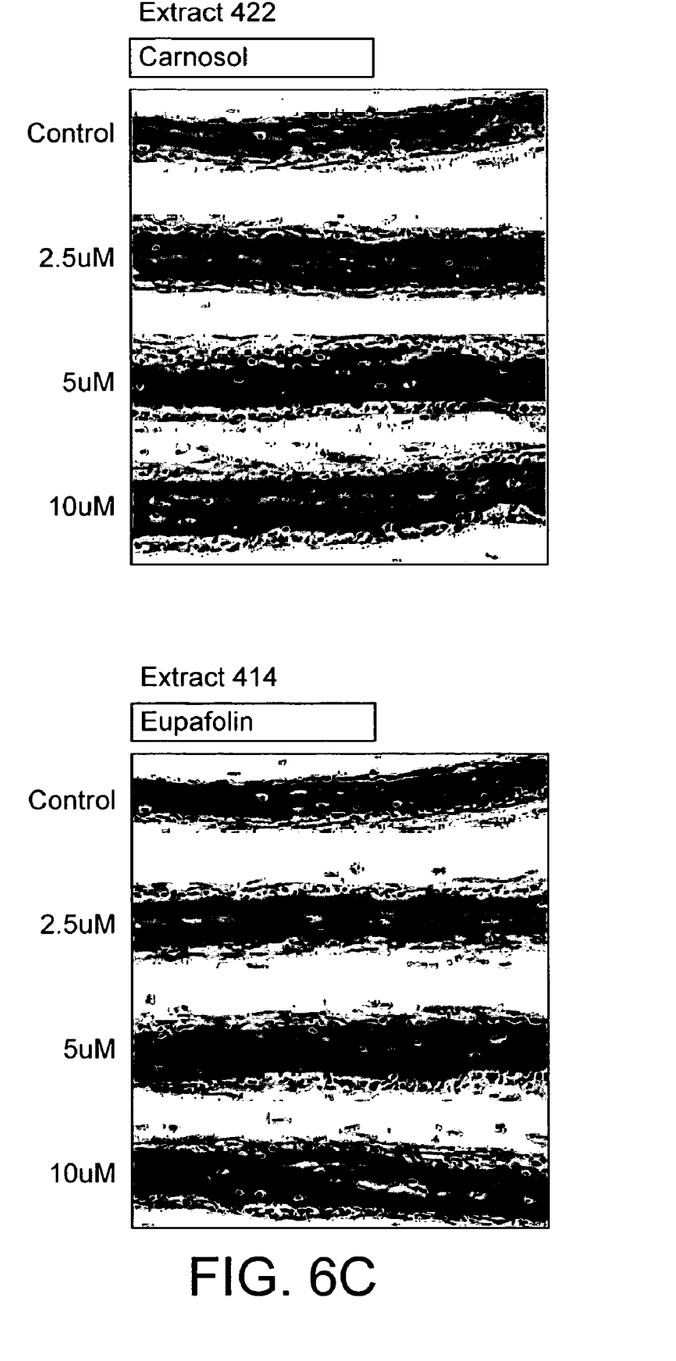
FIG. 6C illustrates an organ culture bone formation: examples with eupafolin and carnosol.

Phenolics active in BMP-2 assay are listed in Table 4. FIGS. 6A-C show certain phenolics positive in bone formation assays.

TABLE 4

Phenolics active in BMP-2, ALP and organ culture assays:

| Flavonoid | BMP-2 induction | ALP activity induction | Bone formation in organ culture |
|---|---|---|---|
| Eupafolin | 3-8X 2.5-10 µM | 2X, 4X 5, 10 µM | Yes |
| Carnosol | 4.5-7X 2.5-10 µM | 2X 2.5-10 µM | Yes |
| Scutellarein | 3-4X 5, 10 µM | 2X 10 µM | Yes |
| Kaempferol | 2.5X 1-10 µM | 2-4X 2.5-10 µM | Yes |
| Acacetin | 5.5X 5-10 µM | 2X 5-10 µM | Slight |
| Genkwanin | 4X 5 µM | 1.5X 10 µM | Slight |

Analysis of BMP-2 Active Rosemary Extracts

The extract for analysis was chosen following previous results showing that the bone formation activity was concentrated in ethyl acetate extracts prepared from a methanol/water extract with (2189) or without enzymatic hydrolysis (2188), (see FIG. 4).

The ethyl extract acetate 2188 was selected for a phytochemical study of its main constituents including the identification and the purification of the compounds by HPLC/ELSD/UV/MS. An in-depth phytochemical evaluation was then completed on the Rosemary extract, active on BMP-2 assay. The preliminary results led to the isolation the above identified active compounds.

Nine pure molecules were identified and prepared in order to carry out the evaluation of their biological activity on bone health. Three of them are believed to be new compounds. These compounds are listed in Table 6.

TABLE 6

3 new compounds isolated from rosemary extract 2188

| NAME | AMOUNT (mg) | PURITY (%) |
|---|---|---|
| Dehydroxy rosmarinic acid | 8.7 | 38 |
| 6"-Feruloylnepitrin | 19.9 | 99.9 |
| 6"-Coumaroylnepitrin | 13 | 94 |

Rosemary Extract and its Anti Bone Resorptive Activity

Osteoporosis is a chronic disease characterized by a slow bone loss. Bone is not a dead tissue. On the contrary, it is constantly remodeled with old bone tissue being replaced by new one. This remodeling is controlled by osteoblasts, the cells responsible for bone formation and by osteoclasts, the cells responsible for bone resorption. Usually, there is a tight coupling between bone formation and bone resorption so that no net bone loss occurs. In osteoporosis, this coupling is not perfect as bone loss is more prominent than bone formation. To treat osteoporosis, one can aim at increasing bone formation, at decreasing bone loss or both. In this example, it is shown that rosemary extracts can decrease bone loss.

Osteoclasts, differentiated from human Peripheral Blood Mononuclear Cells (PBMCs), were cultured on slices of bovine bones. Their resorbing activity was monitored by measuring the amount of type I collagen released in the media as they digest bone.

Type I collagen is the main organic molecule of bone. As bone is digested, the mineral phase of bone is dissolved exposing the collagen fibers to the proteolytic activity of matrix metalloproteinases. Once digested, the collagen fibers become soluble and are released in the culture media where their presence can be quantified by ELISA assays-CTX-I assay.

Figure 7:
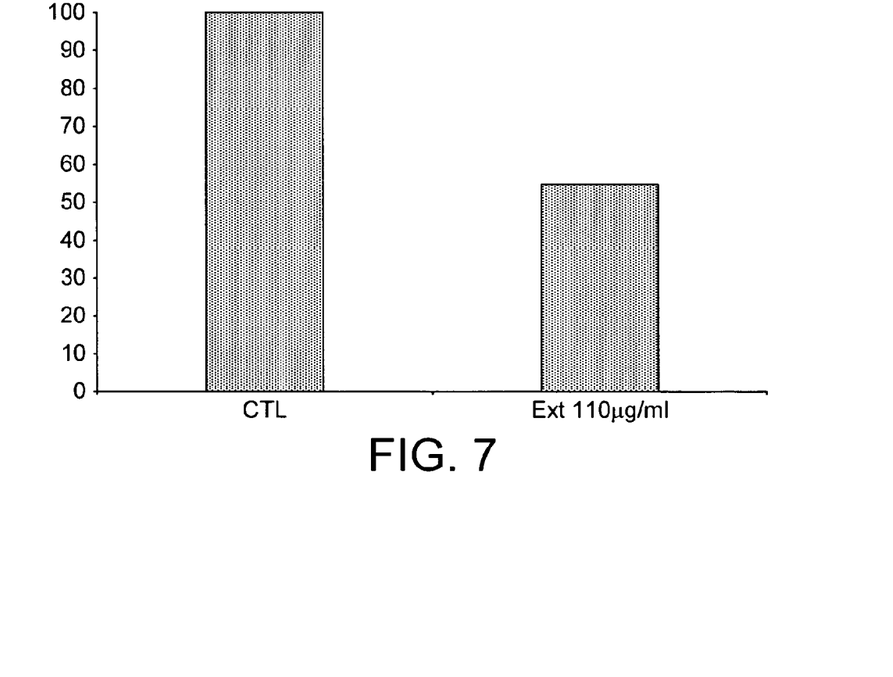
FIG. 7 gives details of the effects of rosemary extract on the activity of human osteoclasts.

FIG. 7 gives details of the effects of rosemary extract on the activity of human osteoclasts as follows: Rosemary extract 1 (extract P31 commercially available from Robertet) at a concentration of 10 µg/ml decreased the amount of type I collagen released from bone slices compared to culture media alone (control (CTL)) (FIG. 8A).

Osteopontin (OPN) mRNA Induction:

Cell culture—HPOBTert osteoblasts were seeded on collagen-coated plates and grown in MEM Eagle α Modification medium supplemented with 10% fetal bovine serum, 1% L-glutamine and penicillin/streptomycin, 1 mM β-glycerolphosphate and 50 µg/ml ascorbic acid in a humidified atmosphere of 5% CO2, and 95% air at 37° C. When carnosol and inhibitors were added, an equivalent amount of Me$_2$SO was used as a vehicle control.

Analysis of mRNA levels by Real-Time PCR—Total cellular RNA was extracted using the NucleoSpin RNA II kit (Macherey-Nagel, Switzerland). Equal amounts (1 µg) of RNA from the different treatments were reverse-transcribed using the First Strand cDNA Synthesis kit for RT-PCR (Roche, Mannheim, Germany). For each sample, 2 µl 10× reaction buffer, 4 µl 25 mM MgCl2, 2 µl nucleotide mix, 2 µl random primers, 1 µl RNAse inhibitor and 0.4 µl AMV reverse transcriptase from the kit were added to the sample. The reverse transcriptase was performed at the following thermal cycling conditions (25° C. for 10 min, 42° C. for 60 min, and 75° C. for 5 min) using the PTC-100™ Concept, Switzerland).

Real-time Quantitative PCR—Quantitative PCR was performed in 25 µl in triplicates. This consisted of 12.5 µl of Taqman 2× Universal PCR Master Mix, 1.25 µl Assay-on-Demand primers and probes (Applied Biosystems, USA) and 6.25 µl RNAse free water. Amplification was conducted in an ABI 7000 machine (Applied Biosystems) with the following thermal profile: 50° C. for 2 min, 10 min at 95° C., followed by 40 cycles of 95° C. for 15 s and 60° C. for 1 min. The gene expression levels were normalised to β-actin expression levels.

Figure 8:
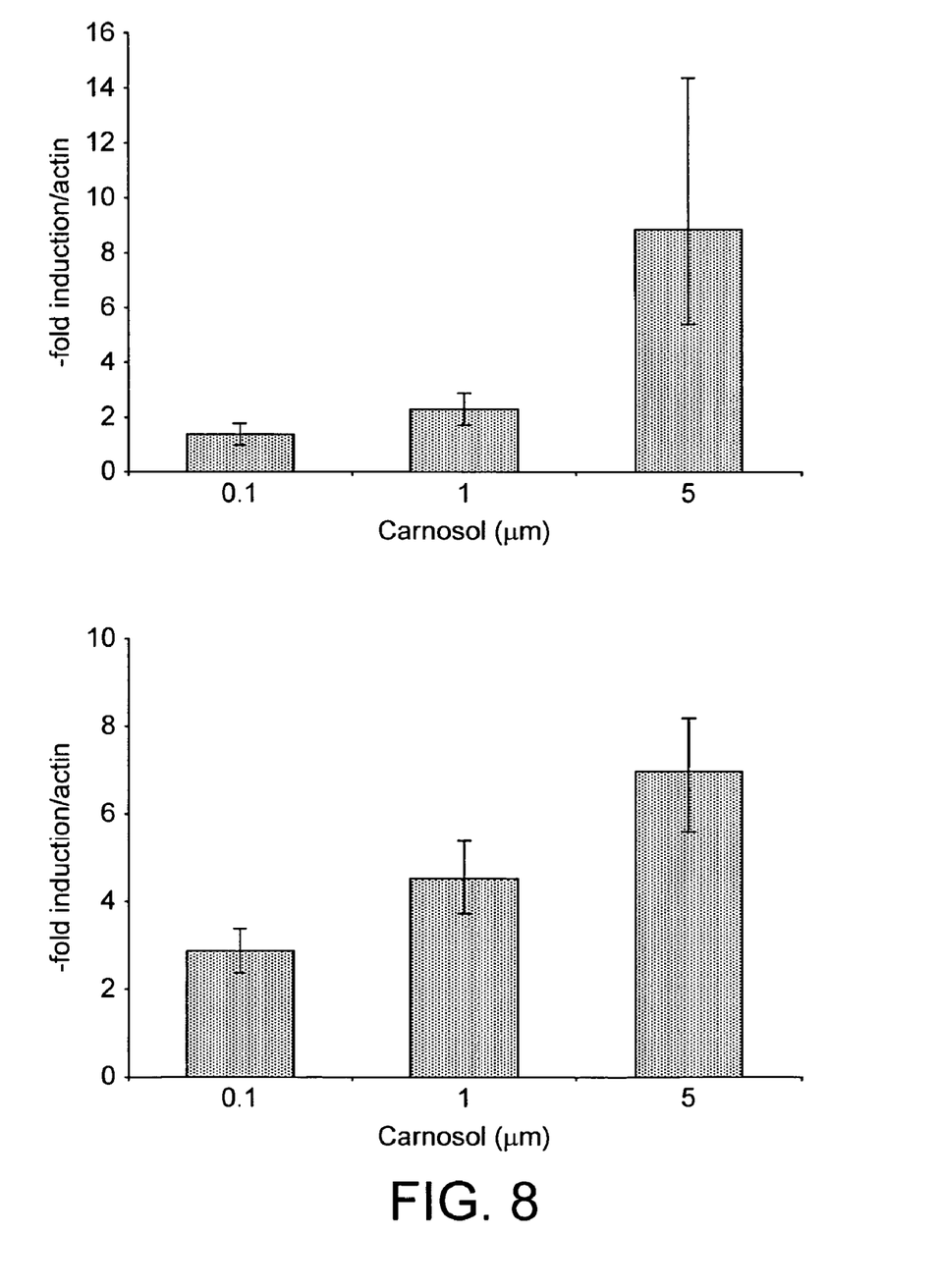
FIG. 8 shows Osteopontin (OPN) mRNA induction in human osteoblast cells (hPOBtert) by rosemary extract or carnosol.

FIG. 8 shows that Rosemary extract or carnosol induce OPN expression dose-dependently by real-time PCR determination of OPN mRNA levels. HPOBtert cells were maintained for 48 h in rosemary extract or carnosol at the indicated doses.

NQO1 induction

Preparation of cytoplasmic extracts—hPOBtert cells were washed two times with cold phosphate-buffered saline and harvested with lysis buffer (1% Triton X-100, 20 mM Tris/HCL pH 8, 137 mM Nacl, 10% Glycerol, 2 mM EDTA pH 8, and freshly added proteinase inhibitors: 1 mM phenylmethylsulfonylfluoride, 0.15 U/ml Aprotinin, 10 µg/ml Leupeptide and 10 µg/ml Pepstatin). The samples were centrifuged at 13000 rpm, 4° C. for 5 min and the supernatant transferred to a fresh tube. The protein concentration was determined using the BioRad protein assay. Approximately 50 µg of each sample were mixed with a suitable volume of sample buffer, denatured for 5 min at 95° C. together with 5 µl protein standard, chilled on ice, and loaded on a 10% ready gel, and submitted to immunoblot analysis using anti-NQO1 antibodies.

Immunoblotting—50 µg of protein cell lysate were resolved by SDS-PAGE. After electrophoresis, proteins were transferred to a PVDF membrane (Invitrogen) according to the manufacturer's protocol. Membranes probed for OPN and NQO1 were blocked and probed in 5% milk in Tris-buffered saline/Tween (20 mM Tris base, pH 7.6, 137 mM, 0.1% Tween 20). The blots were visualised by chemiluminescence development, Western blotting detection system (Amersham Biosciences).

Antibodies—The NQO1 (sc-16464)-specific antibodies were purchased from Santa Cruz Biotechnologies Inc (Santa Cruz, Calif.). The β-actin antibody (A-5441) was purchased from Sigma. The secondary antibodies were purchased from Sigma.

Figure 9:
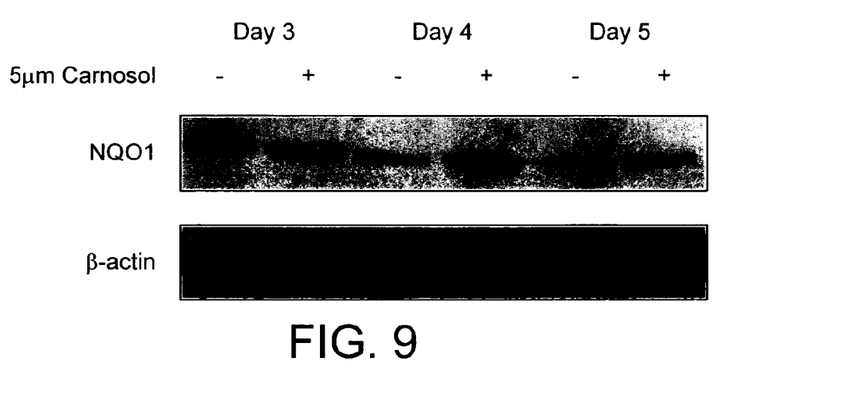
FIG. 9 shows that Carnosol induces the expression of the phase II enzyme NQO1, a typically Nrf-1 regulated gene/protein.

FIG. 9 shows that Carnosol induces the expression of the phase II enzyme NQO1, a typically Nrf-1 regulated gene/protein.

Tolerance testing: A tolerance test was performed in young male Sprague-Dawley rats. The rats were fed orally "by gavage" during 5 days with daily administration of 1 g (extract 2127, MeOH/water) per kg animal body weight. No abnormal behavior, mortality or signs of toxicity were observed during the treatment or the subsequent 10 days observation period. *Rosmarinus officinalis* was therefore considered as safe under these conditions.

Conclusions

Several spice extracts, rich in polyphenols, were found to be positive in the BMP-2 screening assay including *Rosmarinus officinalis Thymus vulgaris* thyme), *Carum carvi*(caraway), and *Mentha spicata* (spearmint). Active extracts from the BMP-2 assay were confirmed in the alkaline phosphatase and organ culture functional assays for bone formation in vitro. Several polyphenolic compounds were identified as responsible for the observed effects.

*Rosmarinus officinalis* (rosemary extract) and *Carum carvi* (caraway), were the most promising extracts, showing bone formation activity in 3 independent bone formation in vitro assays (BMP-2, alkaline phosphatase, bone organ culture) as well as in the calvaria in vivo assay. For example, rosemary extracts stimulated bone formation following injection into murine calvaria in vivo.

Several phenolics that are, e.g., components of rosemary (eupafolin, carnosol, scutellarein, genkwanin, kaempferol, acacetin) are active in the 3 bone formation assays. The most active ones are eupafolin and carnosol. Three new compounds never described previously in the literature were identified.

The presented data also show that the identified polyphenolic compounds from rosemary extract are able to increase bone formation but also to decrease bone resorption. It is not common to find a single compound/extract displaying both properties. This makes these compounds highly interesting candidates to prevent osteoporosis or slow down its progression in humans or pets.

The invention claimed is:

1. A composition comprising a compound selected from the group consisting of,

6"-Feruloylnepitrin,

6"-Coumaroylnepitrin, and a compound with the following formula

Peak-ID II
New
C-0063-W-06 and dehydroxy rosmarinic acid.

2. A method for inducing bone morphogenic protein expression in an individual in need thereof comprising administering to the individual a composition comprising at least one polyphenol.

3. Method in accordance with claim 2 wherein the at least one polyphenol is provided in the form of a plant extract.

4. Method in accordance with claim 2, wherein the polyphenol is selected from the group consisting of a compound selected from the group consisting of, 6"-Feruloylnepitrin, 6"-Coumaroylnepitrin, and a compound with the following formula Peak-ID II
New
C-0063-W-06 and dehydroxy rosmarinic acid, eupafolin, carnosol, scutellarin, genkwanin, kaempferol, acacetin, genkwanin, and mixtures thereof.

5. Method in accordance with claim 3, wherein the plant extract is a rosemary and/or caraway plant extract.

6. Composition in accordance with claim 1, wherein the product is a medicament for humans and/or pets.

7. Composition in accordance with claim 1, wherein the product is selected from the group consisting of a food product, nutritional supplement and nutraceutical for humans and/or pets.

8. Composition in accordance with claim 1, wherein the individual is being treated for osteoporosis.

9. Composition in accordance with claim 1, wherein the individual requires modulation of the ratio of bone formation and/or bone resorption.

10. Composition in accordance with claim 1, wherein the individual requires inhibition of bone resorption.

11. Composition in accordance with claim 1, wherein the individual requires assistance for bone regeneration during fracture healing, increase bone formation and bone mineral density during growth and optimize peak bone mass or to decrease bone loss.

12. Composition in accordance with claim 1, wherein the individual requires improved bone density.

13. Composition in accordance with claim 1 wherein the product comprises the polyphenol in an amount of 0.001-100 wt.-% of the total dry weight of the composition.

14. Composition in accordance with claim 1 wherein the polyphenol is to be administered in amount of 0.01 μg-100 mg per kg body weight per day.

15. Composition in accordance with claim 1 wherein the composition further comprises a protein source, a fat source and a carbohydrate source.

16. Composition in accordance with claim 15 wherein the protein source provides about 1-55% of the total energy of the product, the fat source provides about 5-55% of the total energy of the product, and the carbohydrate source provides about 40-80% of the total energy of the product.

17. Composition in accordance with claim 1 wherein the product is administered orally or internally.

18. Composition in accordance with claim 1 wherein the product is in a form selected from the group consisting of a nutritionally balanced food, a nutritionally complete formula, a dairy product, a chilled or shelf stable beverage, a soup, a nutritional bar, pet food, confectionery, a pharmaceutical composition and combinations thereof.

* * * * *